United States Patent [19]

Kano

[11] 4,099,880
[45] Jul. 11, 1978

[54] METHOD AND AN APPARATUS FOR STEREOSCOPIC MEASUREMENT UTILIZING A THREE-DIMENSIONAL IMAGE

[76] Inventor: Tsutomu Kano, No. 225 Hanakoganei-cho 4-chome, Kodaira-shi, Tokyo, Japan

[21] Appl. No.: 733,967

[22] Filed: Oct. 19, 1976

[30] Foreign Application Priority Data

Aug. 11, 1976 [JP] Japan .......................... 51-107157[U]
Aug. 11, 1976 [JP] Japan .................................. 51-95802
Aug. 11, 1976 [JP] Japan .................................. 51-95803

[51] Int. Cl.² ...................... G01B 9/00; G01B 11/00; G01B 11/24
[52] U.S. Cl. ...................................... 356/164; 356/2; 356/156
[58] Field of Search ...................... 356/162, 164, 1-2, 356/4, 120, 112; 350/136

[56] References Cited

U.S. PATENT DOCUMENTS 4,009,961  3/1977  Maruyama .............................. 356/2

OTHER PUBLICATIONS

Wertheimer et al., "Rapid Contour Generation", Photo-Grammetric Engineering 1974, pp. 467-478.

Primary Examiner—John K. Corbin
Assistant Examiner—Wm. H. Punter
Attorney, Agent, or Firm—William Anthony Drucker

[57] ABSTRACT

A method and apparatus for stereoscopic measurement of an actual value of depth in a subject through its three-dimensional image obtained from two stereoscopically photographed films by utilizing three factors, that is, the center of optical axis of an X-ray tube or a camera which is indexed from the films at the time of stereoscopic photography, distance of movement from the first photographic point to the second photographic point and distance from the X-ray tube or the lens to the film.

4 Claims, 6 Drawing Figures

METHOD AND AN APPARATUS FOR STEREOSCOPIC MEASUREMENT UTILIZING A THREE-DIMENSIONAL IMAGE

BACKGROUND OF THE INVENTION

As a method to obtain a three dimensional image from two stereoscopically photographed films have been known the lenticular method, polarization method, complementary color method, etc by which stereoscopic observation of the three dimensional image is permitted.

Conventionally, the distances in the directions of three dimensional coordinates (axes x, y and z) has been calculated or measured with respect to the three dimensional image which was prepared by the method described above. This procedure was carried out by the following methods, that is, a method of measuring and magnifying the distance on a film or printing paper, a method for measurement by plotting the coordinates of axes X and Y of a scale reduced image on a certain appropriate section paper and diagramming the image in reference to the known and pre-calculated points or a method of measuring the distance based on an image on an optical film. In all these conventional methods, it was necessary to set the known points of the subject on a photographic image to be used and to measure in advance the distances of the above points in the directions of axes x, y and z on the subject. Accordingly, in case of measuring the internal positions of the subjects such as a brain and metallic cast product, that is, the position or distances among several points in the three dimensional space, it was impossible to measure an accurate distance since previous setting of the points which were the reference points for measurement and previous measurement of the distances of the above points in the directions of axes x, y and z were impossible.

On the other hand, it is possible to prepare a three dimensional image and to practise these dimensional measurement which permits accurate measurement of the distance and position on an actual subject by measuring the distance and position of the points on the above three dimensional image; therefore a clear and precise three dimensional image has been required. However, the conventional projector to obtain the three dimensional image is constructed as shown in FIG. 1 and has been unable to provide a clear and precise three dimensional image. In other words, as shown in FIG. 1, the left side film stand 3 and the right side film stand 4 on which the left side film 1 and the right side film 2 stereoscopically photographed are set are required, the left side condenser lens 5 and the right side condenser lens 6 such as Fresnel lenses are arranged below the left and right side film stands 3 and 4 and furthermore the left side light source 7 and the right side light source 8 are provided below the condenser lenses 5 and 6. The left side lens 9 and the right side lens 10 are arranged at the focal positions of the condenser lenses 5 and 6 above the film stands 3 and 4, and the left side first mirror 11 and the right side first mirror 12 which are inclined to 45° to change the optical axis to the horizontal direction are arranged to oppose each other above lenses 9 and 10. The left side second mirror 13 and the right side second mirror 14 are slidably provided at the intermediate positions between the left side first mirror 11 and the right side first mirror 12 to change the direction of the optical axis to the above and the third mirror 16 is arranged to lead the light from the second mirrors 13 and 14 to the screen 15. The left side polarizing filter 17 and the right side polarizing filter 18 which polarize the light passing through the films 1 and 2 are vertically arranged between the first mirrors 11 and 12 and the second mirrors 13 and 14. In the conventional apparatus constructed as described above, when the images of the left side film 1 and the right side film 2 are projected onto the screen 15, the images deviate from each other as shown in FIG. 1. If the second mirrors 13 and 14 are slid to adjust the angle to completely overlap the images and to eliminate such deviation, the images are distorted toward the right and left side peripheries. When such image is viewed through the polarizing glasses, only a three dimensional image with distortion and out-of-focus part can be observed and it cannot be used for accurate three dimensional measurement. In other words, this is because the measured points which are photographed on the right and left side films do not agree on the three dimensional image or are projected deviated from the original positions as the magnification and contraction ratios differ at each part of the image.

SUMMARY

An object of the present invention is to provide a method and an apparatus for easy and accurate measurement of a position or a distance in a three dimensional space, which could not conventionally be measured, based on three dimensional images.

Another object of the present invention is to measure the true value (actual value) of the position on the distance in the three dimensional images obtained from stereoscopic photography of the subject in reference to three basic factors, that is, the center of optical axis of an X-ray tube or a camera which is indexed from the films at the time of stereoscopic photography, distance of movement from the first photographic point to the second photographic point and distance from the X-ray tube or the lenses to the film while observing the above stereoscopically photographed films.

A further object of the invention is to set the center of the optical axis without being skewed on a film at the time of stereoscopic photography and to index it on the film stereoscopically photographed.

A further another object of the invention is to provide a projector having a half mirror so that the clear and precise three dimensional image is obtained by perfectly aligning the optical axes passing through each film.

DETAILED DESCRIPTION OF THE INVENTION

The following describes the measuring method according to the present invention.

Figure 1:
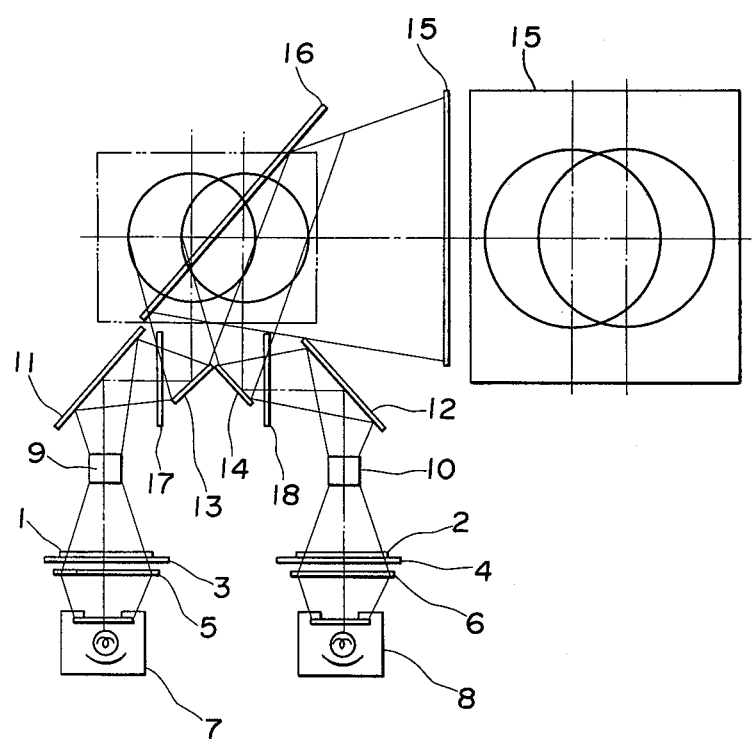
FIG. 1 shows an arrangement of the optical system of the conventional apparatus.
Figure 2:
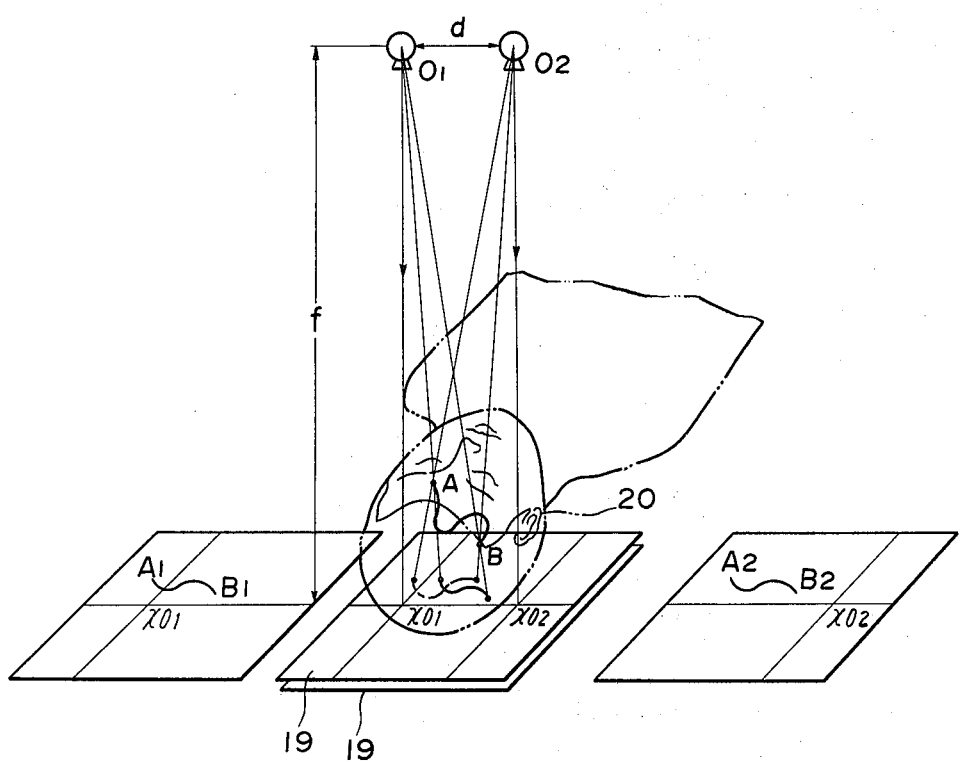
FIG. 2 is a schematic illustration of the apparatus for stereoscopic photography in accordance with the present invention.

In FIG. 2, the distance between the points A and B of the subject 20 arranged above the film 19 is measured. When the X-ray is irradiated onto the subject 20 from the first photographic point $O_1$ as much as the photographic distance $f$ away from the film 19, the image of the point $x_{O1}$ on the perpendicular extending from the first photographic point $O_1$ forms the center of the light axis without being skewed and the points A and B are photographed skewed as the points $A_1$ and $B_1$. Then the film 19 is replaced, the X-ray tube is moved in parallel with the film 19 by distance $d$ from the first photographic point $O_1$ to the second photographic point $O_2$. When the X-ray is irradiated from this second photographic point $O_2$ onto the subject, the image of the point $X_{O2}$ on the perpendicular extending from the second photographic point $O_2$ forms the center of the optical axis without being skewed and the points A and B are photographed skewed as the points $A_2$ and $B_2$. Stereoscopic photography of the subject 20 is carried out by the above procedures and the $O_1$ films are stereoscopically photographed from the positions of the first photographic point $O_1$ and the $O_2$ film stereoscopically photographed from the position of the second photographic point $O_2$ are obtained.

Figure 3:
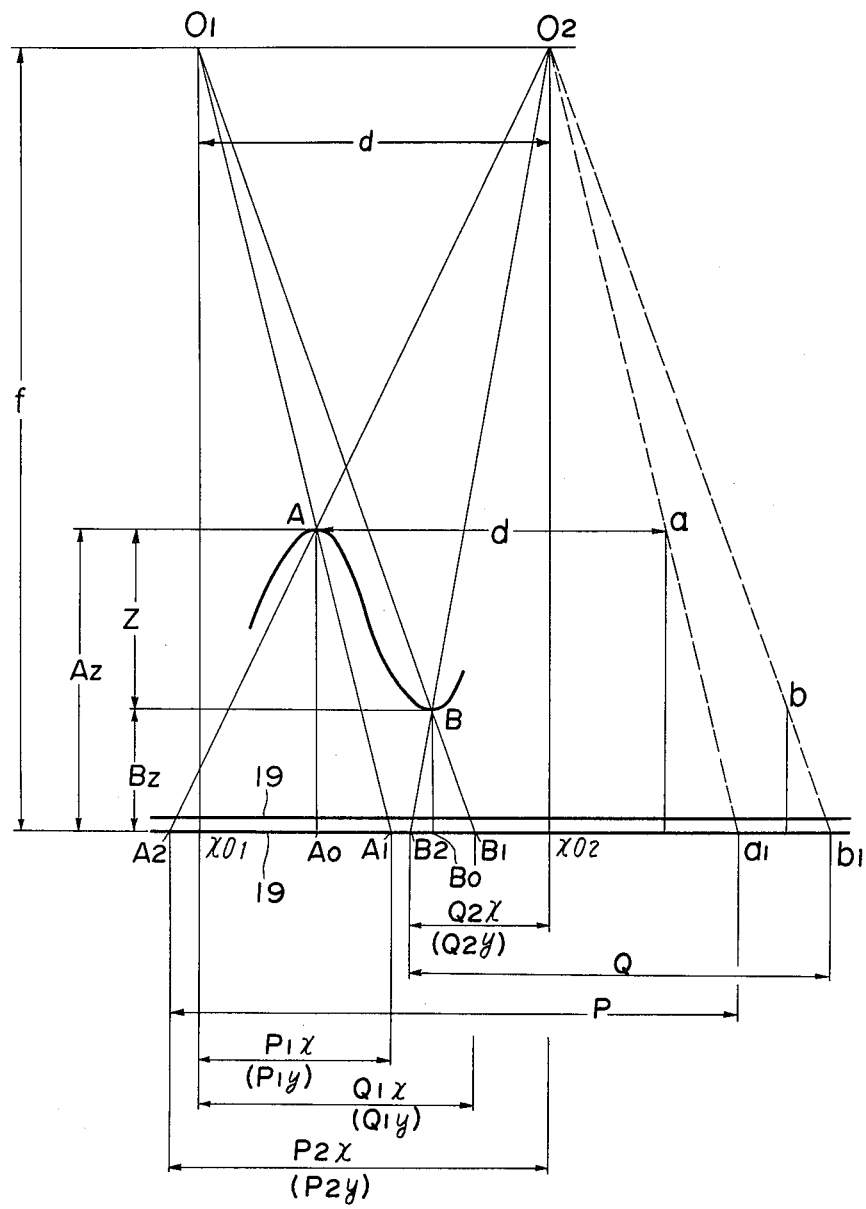
FIG. 3 is a linear diagram for explaining the equations.

In FIG. 3, the points A and B on the $O_1$ film are as follows:

Point A: $\overline{x_{01}A_1} = \overline{x_{01}A_0} + \overline{A_0A_1}$

Point B: $\overline{x_{01}B_1} = \overline{x_{01}B_0} + \overline{B_0B_1}$

In this case, the points $A_0$ and $B_0$ show the positions on the perpendiculars extending from the points A and B on the film 19 but they are not photographed.

The points A and B on the 02 film are as follows:

Point A: $\overline{x_{02}A_2} = \overline{x_{02}A_0} + \overline{A_0A_2}$

Point B: $\overline{x_{02}B_2} = \overline{x_{02}B_0} + \overline{B_0B_2}$

When the first photographic point $0_1$ is superposed on the second photographic point $0_2$, $\overline{0_1 A_1}$ is equal to $\overline{0_2 a_1}$ and the photographic point moves parallel by distance $d$ in parallel with the subject $\overline{0_1 B_1}$ is equal to $\overline{0_2 b_1}$.

Accordingly, $\triangle A A_2 A_1 \sim \triangle O_2 A_2 a_1$ is given.

$$\overline{O_2 x_{02}} : \overline{A_2 a_1} = \overline{A A_0} : \overline{A_2 A_1}$$

In the above equation, $\overline{O_2 x_{02}}$ is the photographic distance $f$ given as $\overline{O_2 x_{02}} = f$.

If $\overline{A_2 a_1} = P$ is given, the following relationship is obtained.

$$\overline{A_2 A_1} = \overline{A_2 a_1} - d = P - d$$

If the height of the point A from the film 19 is $\overline{A A_O} = x$, the following is given.

$$f : P = x : (P - d)$$

$$P \cdot x = f \cdot (P - d)$$

$$x = \frac{f \cdot (P - d)}{P}$$

From $\triangle B B_2 B_1 \sim \triangle O_2 B_2 b_1$, the following is obtained.

$$\overline{O_2 x_{02}} : \overline{B_2 b_1} = \overline{B B_0} : \overline{B_2 B_1}$$

In the above equation, $\overline{O_2 x_{02}}$ is the photographic distance $f$ given as $\overline{O_2 x_{02}} = f$.

If $\overline{B_2 b_1} = Q$ is given, $$\overline{B_2 B_1} = \overline{B_2 b_1} - d = Q - d$$

If the height of the point B from the film 19 is $\overline{B B_O} = y$, the following is given.

$$f : Q = y : (Q - d)$$

$$Q \cdot y = f(Q - d)$$

$$y = \frac{f(Q - d)}{Q}$$

In FIG. 3, the distance (depth) $z$ between the points A and B in the direction of axis $z$ is given as follows:

$$Z = \overline{A A_0} - \overline{B B_0} = \frac{f(P - d)}{P} - \frac{f(Q - d)}{Q} = \frac{f(P - d) - f(Q - d)}{P \cdot Q}$$

Accordingly, the distance (depth) of any point on the film 19 in the direction of axis $z$ can be measured by measuring values P and Q and substitute the measured values to the above expression of relation.

Then the distance $\overline{A_0 B_0}$ between the points A and B in the direction of axis $x$ is to be obtained. The center of the optical axis is photographed just below the perpendicular extending from the X-ray tube without being skewed and the images of other points are differently skewed, depending on the depths and positions. Since the distances of all points in the direction of axis $z$ can be measured accurately as described above, the distance in the direction of axis $x$ can be expressed as a function of the distance from the center of the optical axis and the distance in the direction of axis $z$.

In FIG. 3, the following expressions are given:

$$\overline{A A_0} = A_z = \frac{f(P - d)}{P} \quad (1)$$

$$\overline{B B_0} = B_z = \frac{f(Q - d)}{Q} \quad (2)$$

$$\overline{A_0 B_0} = \overline{A_0 x_{02}} - \overline{B_0 x_{02}} \quad (3)$$

Since $\triangle A A_0 A_2$ and $\triangle O_2 x_{02} A_2$ are a right triangle respectively and have the angle $\angle O_2 A_2 x_{02}$ in common, the following is obtained.

$$\triangle A A_0 A_2 \sim \triangle O_2 x_{02} A_2 \quad (4)$$

$$\overline{A_0 x_{02}} = \overline{A_2 x_{02}} - \overline{A_2 A_0}$$

From from the equation (4), $f : A_z = P_{2x} : \overline{A_2 A_0}$ ($P_{2x} = A_2 x_{02}$) is obtained.

$$\overline{A_2 A_0} = \frac{A_z \cdot P_{2x}}{f}$$

$$\therefore \overline{A_0 x_{O2}} = P_{2x} - \frac{A_z \cdot P_{2x}}{f}$$

Similarly, $$\Delta B B_2 B_0 \sim \Delta O_2 B_2 x_{O2} \quad (5)$$

$$\overline{B_0 x_{O2}} = \overline{B_2 x_{O2}} - \overline{B_2 B_0}$$

From the equation (5), $f : B_z = Q 2x : \overline{B_2 B_0} (Q_{2x} = \overline{B_2 x_{O2}})$ is obtained.

$$\overline{B_2 B_0} = \frac{B_z \cdot Q_{2x}}{f}$$

$$\overline{B_0 x_{O2}} = Q_{2x} - \frac{B_z \cdot Q_{2x}}{f}$$

If the above equations are substituted in the equation (3), the following is obtained.

$$\overline{A_0 B_0} = X = (P_{2x} - \frac{A_z \cdot P_{2x}}{f}) - (Q_{2x} - \frac{B_z \cdot Q_{2x}}{f})$$

Then, the distance Y between the points A and B in the direction of axis $y$ is to be obtained. This distance is obtained in the same method as the distance in the direction of axis $x$ described above on the assumption that the film 19 is turned by 90° in FIG. 3.

$$Y = (P_{2y} - \frac{A_z \cdot P_{2y}}{f}) - (Q_{2y} - \frac{B_z \cdot Q_{2y}}{f})$$

Where, $P_{2y}$: distance of the image of point A from the point $x_{O2}$ in the direction of axis $y$ $Q_{2y}$: distance of the image of point B from the point $x_{O2}$ in the direction of axis $y$ Then, the linear distance L (true value) between the points A and B is to be obtained. Value L is expressed as a function of values Z, X and Y described in the foregoing and given as below.

$$L = \sqrt{X^2 + Y^2 + Z^2}$$

As described above, the distance between the points A and B on the subject 20 in the three dimensional directions is measured using the functions of the distance d between the first photographic point $O_1$ and the second photographic point $O_2$, photographic distance $f$ between the X-ray tube and the film 19 and distances from the center points $x_{O1}$ and $x_{O2}$ of the optical axes to each image at the measured point. Accordingly, it is necessary to obtain the center of the optical axis on the photographed film 19. The following describes a method of obtaining the center point of the optical axis.

Figure 4:
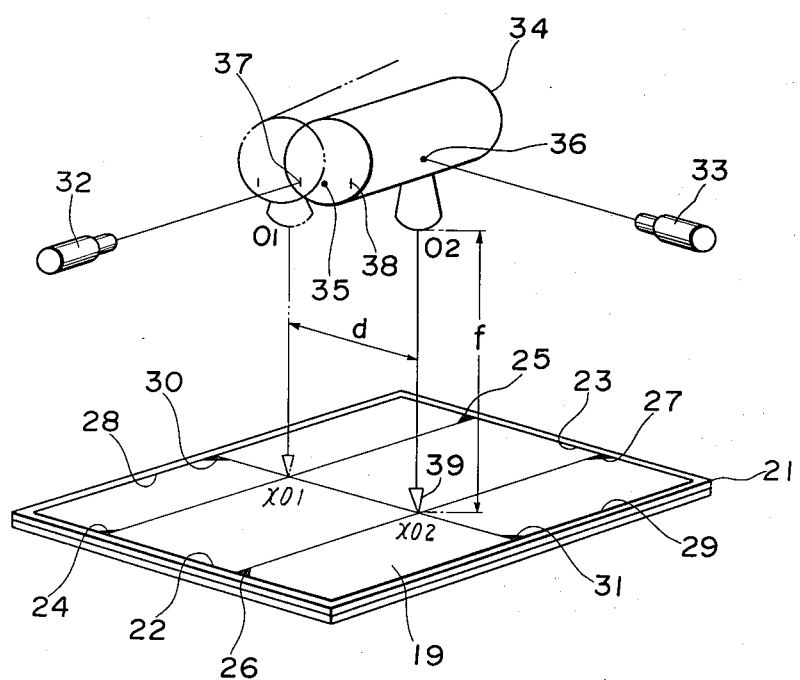
FIG. 4 is a perspective view of a preferable embodiment of the film holder.

Based on the photographed films, the position of the center of the optical axis can be calculated by realizing the relative positions of three factors, the X-ray tube, subject and films, based on two stereoscopically photographed films if the subject is available. In general cases, however, only the films are available and the subject is unavailable. Therefore, the photography is performed with the film holder 21 as shown in FIG. 4 at the time of photography. The film holder 21 is made up by hinging two frames, and two indicators 24, 25 and 26, 27 are provided on each of opposing sides 22 and 23 of the upper frame so that the indicators can slide along the sides and one of similar indicators 30 and 31 is provided on each of opposing other sides 28 and 29 of the upper frame. These indicators 24, 25, 26, 27, 30 and 31 are made of material such as lead which does not admit the X-ray in case of the X-ray photography.

Before the photography, the following operations are to be performed. In the X-ray room, the beams are emitted into the X-ray tube 34 from two beam sources 32 and 34 provided at the specified height so that the optical axes intersect orthogonally each other and the X-ray tube 34 is positioned so that the beams pass through two center marks 35 and 36 on the outer peripheral surface and the end face of the outer casing of the X-ray tube 34 which indicates the center of the X-ray tube. While one beam is kept passing through the center mark 36 on the outer peripheral surface of the outer casing of the X-ray tube 34, the X-ray tube 34 is moved in parallel by $d/2$. This operation is carried out by superposing one (37) of two optical axis marks 37 and 38 indicated with a distance of $d/2$ at both sides of the center mark 35 inscribed on the end surface of the outer casing of the X-ray tube with the other beam. At this position, that is, the first photographic point $O_1$, the weight 39 is suspended from the center of the X-ray tube toward the film holder 21. The indicators 24, 25, 30 and 31 are slid and fixed so that the line between the indicators 24 and 25 of the film holder 21 intersects the line between the indicators 30 and 31 at the position marked by the weight 39. This intersection indicates the center $x_{O1}$ of one optical axis. Then the X-ray tube 34 is moved parallel by $d$ in the reverse direction to the above case. The direction of this movement is parallel with the line between the indicators 30 and 31 and this operation is performed by aligning one beam with one optical axis mark 38 different from that described above while the other beam is kept aligned with the center mark 36 inscribed on the outer peripheral surface of the outer casing of X-ray tube 34. At this position, that is, the second photographic point $O_2$, the weight 39 is suspended from the center of the X-ray tube toward the film holder 21. The indicators 26 and 27 are moved and fixed so that the line between the indicators 26 and 27 of the film holder 21 intersects the line between the indicators 30 and 31 at the position marked by the weight 39. This intersection indicates the center point $x_{O2}$ of the other optical axis. After thus determining the first and second photographic points $O_1$ and $O_2$ and the center points $x_{O1}$ and $x_{O2}$ of the optical axis, the film 19 is set on the film holder 21 and the subject is mounted thereon. The $O_1$ film is obtained by irradiating the X-ray to the subject from the first photographic point. When the film is replaced without moving the subject and the X-ray is irradiated onto the subject from the second photographic point $O_2$, the $O_2$ film is obtained. The indicators are photographed with the subject on the $O_1$ and $O_2$ films and indicate the centers of two optical axes as described above.

Figure 5:
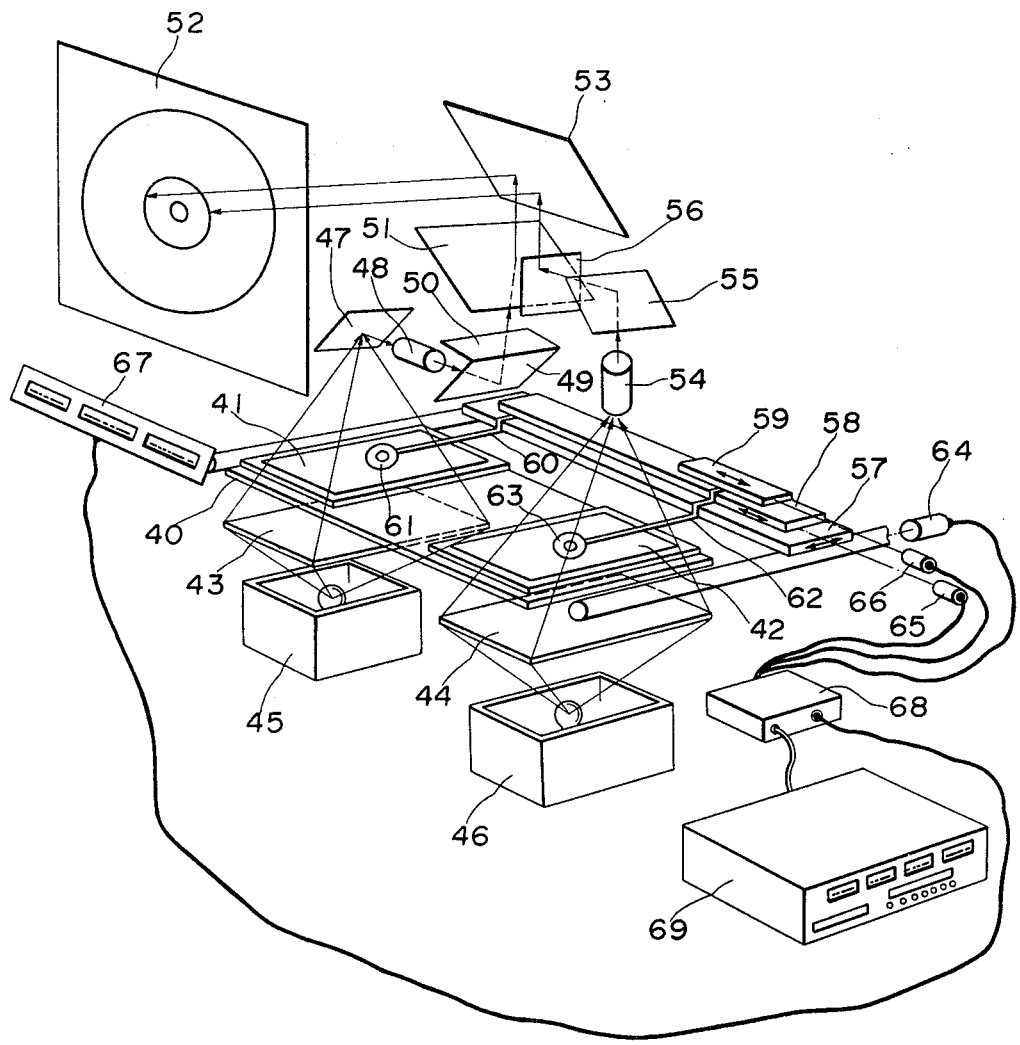
FIG. 5 is a diagram describing the principle of a preferable embodiment of the apparatus in accordance of the present invention.
Figure 6:
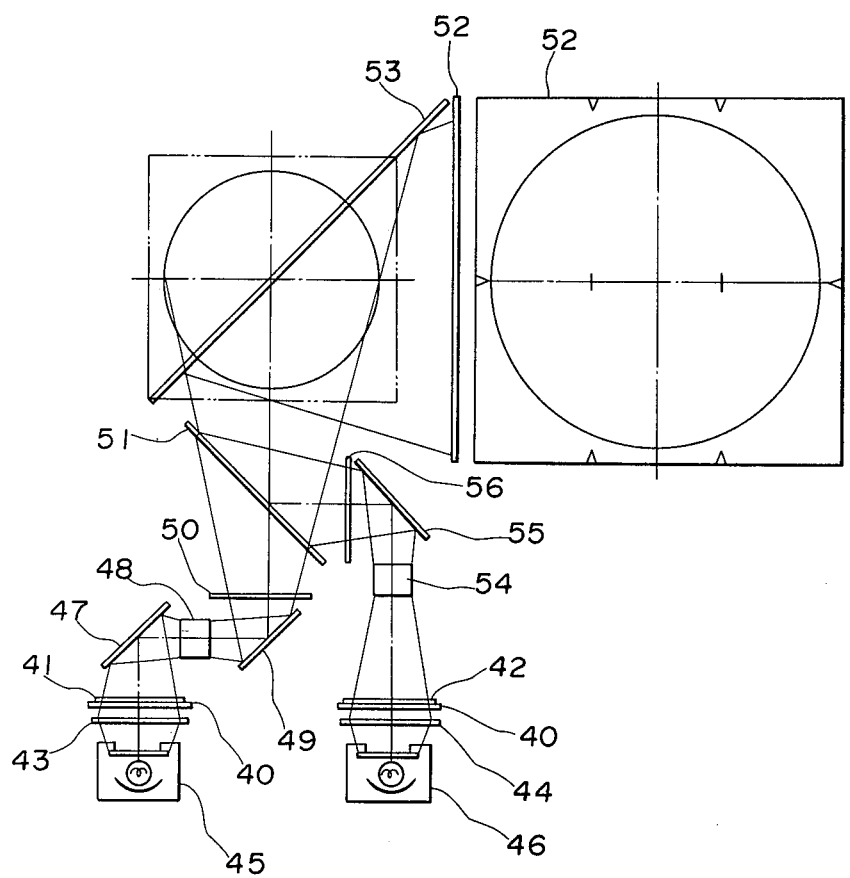
FIG. 6 shows an arrangement of the optical system in accordance with the present invention.

The following describes the apparatus which performs the measurement by the stereoscopic photography using two films prepared as described above. FIG. 5 shows the principle of the apparatus. The film stand 40 is constructed so that the $O_1$ film 41 and $O_2$ film 42 are set in parallel arrangement. Two Fresnel lenses 43 and 44 are provided below the film stand 40 and two light sources 45 and 46 are provided further below the Fresnel lenses 43, 44. The light sources 45 and 46 preferably employs the xenon lamps to absorb heat but are not restricted by this preference. The left side first mirror 47 is provided with inclination at 45° above the $O_1$ film 41 to change the direction of the light to the horizontal direction. The left side lens 48 which receives the light from the left side first mirror 47 is provided at the focal position of the Fresnel lens 43, magnifies the image and leads the light to the left side second mirror 49. The left side second mirror 49 is provided in parallel with the left side first mirror 47 to change the light to the vertical direction. The left side polarizing filter 50 is horizontally provided above the left side second mirror 49 and the half mirror 51 is provided with inclination of 45° above the left side polarizing filter 50. The third mirror 53 is provided with inclination of 45° above the half mirror 51 to lead the light to the screen 52 provided at the front side. The right side lens 54 is vertically provided at the focal position of the Fresnel lens above the $O_2$ film 42 and the right side first mirror 55 is provided with inclination of 45° above the right side lens 54 to change the light to the horizontal direction and to lead it to the half mirror 51. The right side polarizing filter 56 is vertically provided at an intermediate position between the right side first mirror 55 and the half mirror 51. The left side polarizing filter 50 and the right side polarizing filter 56 are mounted so that they are rotated respectively at different 90° angle. The y-axis table 57 which is slid to forward and backward is provided in a plane parallel with the film stand 40 and the x-axis table 58 which moves orthogonally against the movement of the y-axis table is provided above the y-axis table 57. Furthermore, the z-axis table 59 which moves in the same direction as the x-axis table 58 is provided above the x-axis table.

The left side marker 61 is fixed to the tip end of the arm 60 which is fixed on the x-axis table 58 to slide on the $O_1$ film. The right side marker 63 is fixed to the tip end of the arm 62 which is fixed on the z-axis table 59 to slide on the $O_2$ film 42. Accordingly, the left side marker 61 and the right side marker 63 operate differently only when the z-axis table 59 is driven and the distance between the left side marker 61 and the right side marker 63 increases or decreases. In other case, the left side marker is operated with the right side marker. The above-mentioned tables 57, 58 and 59 are moved through the feed screws (not shown) which are rotated by the motor (not shown) though it does not mean that their movements are limited. The feed screws are provided with the rotary encoders 64, 65 and 66 and the amounts of movement of the tables 57, 58 and 59 can be known by counting the numbers of pulses generated from the rotary encoders 64, 65 and 66. The rotary encoders 64, 65 and 66 are connected to the data processor 68 which is connected to the digital indicator 67 indicating the measured values on the films 41 and 42, while said data processor 68 is connected to the micro computer 69 capable of calculating based on the input and digital-indicating the results of calculation. The micro computer 69 performs calculations based on the equations described in the foregoing and displays values Z X Y and L (true values).

The following describes the operation of the apparatus in accordance with the present invention. The $O_1$ film 41 and the $O_2$ film 42 are set in parallel arrangement at the specified positions on the film stand 40. When the left side light source 45 emits a light, the light passes through the left side Fresnel lens 43 and the left side film 41, changes its axial direction to the horizontal direction by being reflected at the left side first mirror 47 and is condensed to the left side lens 48. The light which is condensed to and passes through the left side lens 48 is reflected by the left side second mirror 49 to change its axial direction to the vertical direction and a light of special phase is eliminated by hte left side polarizing filter 50. Furthermore this light passes through the half mirror 51 from the rear side to the front side with slight refraction. On the other hand, when the right side light source 46 emits a light, the light passes through the right side Fresnel lens 44 and the right side film 42 and is condensed to the right side lens 54. The light which is condensed to and passes through the right side lens 54 is reflected by the right side first mirror 55 to change its axial direction to the horizontal direction and reaches the right side polarizing filter 56, where the light of special phase is eliminated. Furthermore the light reaches the half mirror 51 and is reflected thereon. At this time, the optical axis is aligned with the optical axis of the light coming from the rear side of the half mirror 51 through the left side film 41, and the light reaches the third mirror 53 together with the light coming from the rear side of the half mirror 51 and is reflected by the third mirror 53. Accordingly, the images of the left side film 41 and the right side film 42 are completely overlapped, magnified and projected onto the screen 52. When this overlapped image is viewed through a pair of polarizing glasses of which the rotation angle is made different by 90° at the left side and the right side, the left side eye can see the image of the left side film 41 and the right side eye can see the image of the right side film 42 and thus a clear and precise three dimensional image can be obtained.

The y-axis table 57 and the x-axis table 58 are moved while observing the three dimensional image and the left side marker 61 is aligned with the center point $x_{O1}$ of the optical axis of the film 41. Then the z-axis table 59 is moved and the right side marker 63 is aligned with the center point $x_{O2}$ of the optical axis of the $O_2$ film 42. Thus, the markers 61 and 63 are set at the center points $x_{O1}$ and $x_{O2}$ of the optical axis and the displays 67 and 69 are reset to make the values of three axes zero. Then the tables 57, 58 and 59 are moved to align the markers 61 and 63 with the first measuring point A in the three dimensional image while observing the three dimensional image. Under this condition, the left side marker 61 is aligned with the point $A_1$ (FIG. 3) on the $O_1$ film 41 and the right side marker 63 with the point $A_2$ (FIG. 3) on the $O_2$ film 42, and the amount of movement in three axial directions is calculated and displayed. In FIG. 3, $\overline{x_{O1}A_1}(=\overline{x_{O2}a_1})$ and $\overline{x_{O2}A_2}$ are measured and the following is obtained.

$$\overline{A_2 a_1} = P = \overline{x_{O2}A_2} + \overline{x_{O2}a_1}$$

When the distance $d(=\overline{x_{O1}x_{O2}})$ between the first photographic point $O_1$ and the second photographic point $O_2$ and the distance $f$ between the X-ray tube and the films are inputted in the micro computer 69, the following values are calculated, $$\overline{AA_0} = A_z = \frac{f(P-d)}{P}$$

$$\overline{A_0 x_{01}} = P_{1x} - \frac{A_z \cdot P_{1x}}{f}$$

$$\overline{A_0 y_{01}} = P_{1y} - \frac{A_z \cdot P_{1y}}{f}$$

where, $A_O Y_{O1}$ is a distance between the center point $x_{O1}$ of the optical axis and the point $A_O$ in the direction of axis $y$, and moreover the following is calculated and $$L = \sqrt{A_z^2 + \overline{A_O x_{O1}}^2 + \overline{A_O Y_{O1}}^2}$$

digital-displayed on the micro computer 69.

Then, the measured values and calculated values are stored in the memory of the micro computer 69 and the reference operation for determing this first measuring point A as the reference point is performed. By this operation, the displays of the micro computer 69 are reset to 0 (zero) and therefore the displays always indicate 0 when the left side and right side markers 61 and 63 are aligned with the first measuring point A.

When the markers 61 and 63 are moved to the second measuring point B, $\overline{x_{O1} B_1}(= \overline{x_{O2} b_1})$ and $\overline{x_{O2} A_2}$ are measured and the following obtained. $B_2 b_1 = Q = \overline{x_{O2} B_2} + \overline{x_{O2} b_1}$ (See FIG. 3.)

In the micro computer 69, the following values are calculated, $$\overline{B B_0} = B_z = \frac{f(Q - d)}{Q}$$

$$\overline{B_0 x_{O1}} = Q_{1x} - \frac{B_z \cdot Q_{1x}}{f}$$

$$\overline{B_0 y_{O1}} = Q_{1y} - \frac{B_z \cdot Q_{1y}}{f}$$

where, $B_O y_{O1}$ is the distance from the center point $x_{O1}$ of the optical axis to point $B_O$ in the direction of axis $y$.

$$L = \sqrt{B_z^2 + \overline{B_O x_{O1}}^2 + \overline{B_O Y_{O1}}^2}$$

and the following values based on the first measuring point A as the reference point are calculated and displayed on the displays of the micro computer 69.

$$Z = A_z - B_z$$

$$\overline{A_0 B_0} X = (P_{1x} - \frac{A_z \cdot P_{1x}}{f}) - (Q_{1x} - \frac{B_z \cdot Q_{1x}}{f})$$

$$Y = (P_{1y} - \frac{A_z \cdot P_{1y}}{f}) - (Q_{1y} - \frac{B_z \cdot Q_{1y}}{f})$$

$$L = \sqrt{Z^2 + X^2 + Y^2}$$

These values can be sotred in the memory of the micro computer 69. When the markers 61 and 63 are moved to the third measuring point C, the distances X, Y and Z in the three dimensional directions of axes from the first measuring point A and the linear distance (true value) L can be measured. When the reference operation is performed at an arbitrary measuring point, the reference point moves to the said measuring point and subsequently the distances from the said point are measured.

As described above, the three dimensional measurement by the method and the apparatus in accordance with the present invention is carried out by aligning the left side and right side markers 61 and 63 with the center point $x_{O1}$ and $x_{O2}$ of the optical axis before aligning the markers 61 and 63 with the three dimensional image projected on the screen 52 and driving the tables 57, 58 and 59 to move the markers 61 and 63 to the first measuring point A after resetting the digital displays to zero. The distance of movement in each axial direction is digitally displayed on the displays for the axes $x$, $y$ and $z$. When the markers 61 and 63 are moved to the second measuring point B after the distance of movement has been stored in the memory and the reference operation has been performed, the distance of movement from the center points $x_{O1}$ and $x_{O2}$ of the optical axis to the second measuring point B can be measured. With the results of measurement substituted into the equations for calculation, the true distance from an arbitrary measuring point A (O, O, O) to the measuring point B (x, y, z) can be measured.

The above describes the measurement using two X-ray films which are stereoscopically photographed. This measurement can be carried out similarly with an ordinary camera. In other words, the first photographic point $O_1$ and the second photographic point $O_2$ are the centers of the left side and right side lenses for the ordinary camera. The distance from the centers of the lenses recorded on the films to the images at the arbitrary points on the films are measured in the same manner or by the same means as described above by recording the centers of lenses on the left side and right side films, and the position or the actual distances among several points in the three dimensional space can be obtained by utilizing the distance between the centers of lenses and the distance between the lenses and the films in photography.

As described in the foregoing, the present invention permits measurement of the actual distance between the arbitrary points in the three dimensional space with the three dimensional images prepared from two stereoscopically photographed by calculating the data during the photography, that is, distance d between the first photographic point $O_1$ and the second photographic point $O_2$, distance f from the X-ray tube to the film and distances from the center points $x_{O1}$ and $x_{O2}$ of the optical axis at the arbitrary points on the films which are measured while observing the three dimensional images. In other words, in case of the present invention, the distance between the specified points which is set in advance need not be measured in advance. Accordingly, the method of measurement in accordance with the present invention is highly effective for diagnosing an affected part in a human body. The shape and position of the affected part can be accurately measured in advance before operation and therefore the operation can be performed precisely and efficiently. Moreover, the recovery of the affected part after operation can be easily checked and diagnosed and the present invention will exhibit a great contribution in the field of medicine. In industrial application, this method and apparatus will be advantageous in detection of internal defects of cast products, easy inspection of qualities without destroying the products since the shape and position of defects can be known from the outside, inspection of parts in the plants without stopping the operation and destroying the parts, prevention of accidents and troubles and great saving of costs for employees and materials necessary for inspection.

In the apparatus in accordance with the present invention, the left side marker 61 is attached with the arm 60 to the x-axis table 58 provided on the y-axis table 57 and the right side marker 63 is attached with the arm 62 to the z-axis table 59 which is provided on the x-axis table 58 and moves in the same direction as the x-axis table; therefore the parallax measurement in the direction of axis x can be easily performed. Since the movement and the amount of movement can be measured merely by providing the feed screws and the motors on the tables 57, 58 and 59 and attaching the rotary encoders to the feed screws, the contruction can be simple and the calculation of actual values can be facilitated.

What is claimed is:

1. A method for measurement of actual distances in three dimensional axes using a three dimensional image in a three dimensional measurement with a three dimensional image obtained from two stereoscopically photographed films of a subject and a distance between centers of an optical axis and a distance between a light source and film, wherein said three dimensional image is prepared with a first film in which a center of a first optical axis is recorded and a second film in which a center of a second optical axis is recorded, a first marker which slides on said first film is moved to align with the center of the first optical axis of the first film, a second marker which slides on said second film is moved to align with the center of the second optical axis of said film, said first and second markers are moved to a first measuring point to align the first and second markers with said first measuring point on the three dimensional image, distances from said first measuring point to said center of the first optical axis and center of the second optical axis in directions of axes $x$, $y$ and $z$ are measured, calculated and recorded, the first and second markers are moved to a second measuring point to align on the three dimensional image, and distances from said second measuring point to said center of the first optical axis and said center of the second optical axis in directions of axes $x$, $y$ and $z$ are measured, calculated and recorded to measure linear distances between two points.

2. An appratus for measurement of actual distances in three dimensional axes using a three dimensional image comprising a y-axis table which is moved by a first motor in a linear direction in a plane parallel with a film stand, a means to measure an amount of movement of said y-axis table, an x-axis table which is provided on said y-axis table and moved by a second motor in a direction orthogonally intersecting the direction of movement of the y-axis table, a means to measure an amout of movement of said x-axis table, a z-axis table which is provided on said x-axis table and moved by a third motor in the same direction as the x-axis table, a means to measure an amount of movement of said z-axis table, a first marker which is provided with the x-axis table to slide on said first film and a second marker which is provided with the z-axis table to slide on said second film in a three dimensional image projector comprising a film stand on which the first and second stereoscopically photographed films can be set in parallel arrangement, a light source which irradiates a light onto said first and second films through respective condenser lenses and a means consisting of mirrors and lenses so that images of the first and second films are aligned and focussed on a screen.

3. An apparatus for measurement of actual distances in three dimensional axes using a three dimensional image in accordance with clam 2, wherein a film holder for stereoscopic photography comprises a frame, a pair of indicators which are slidably provided at peripheral parts of said frame which oppose each other and two pairs of indicators which are slidably provided at other peripheral parts of said frame which oppose each other.

4. An apparatus for measurement of actual distances in three dimensional axes using a three dimensional image in accordance with claim 2, wherein said three dimensional image projector comprises a light source which irradiates a light to said first and second stereoscopically photographed films respectively, a means consisting of mirrors and lenses which are adapted to orthogonally intersect an optical axis of light passing through said first film and an optical axis of light passing through said second film, a half mirror which is provided at an intersection of said both optical axes so that said half mirror intersects each of said both optical axes at an angle of 45° and a screen which receives a light which passes through said half mirror and is reflected by said half mirror and forms thereon images photographed in said first and second films.

* * * * *